United States Patent
Krosney et al.

(10) Patent No.: US 6,787,782 B1
(45) Date of Patent: Sep. 7, 2004

(54) ULTRAVIOLET-LIGHT VEHICLE AIR CLEANING SYSTEM

(75) Inventors: Mark D. Krosney, Miami, FL (US); Joseph Baughman, Summersville, WV (US); Richard L. Rauckhorst, III, Summersville, WV (US); Michael G. Casto, Canvas, WV (US); Tolek Pawelko, Deer Park, NY (US); Jennifer L. Gloisten, Farmingville, NY (US); William E. Reisenauer, Commack, NY (US)

(73) Assignee: B/E Aerospace, Inc., Wellington, FL (US)

( * ) Notice: Subject to any disclaimer, the term of this patent is extended or adjusted under 35 U.S.C. 154(b) by 0 days.

(21) Appl. No.: 10/421,296

(22) Filed: Apr. 23, 2003

(51) Int. Cl.[7] .................... G01N 21/01; G01N 21/51; G01N 23/10; G01N 23/12
(52) U.S. Cl. .................... 250/436; 250/435; 250/432 R; 454/158
(58) Field of Search .................... 250/435, 455.11, 250/474.1, 372, 472.1, 473.1, 482.1, 432 R, 436; 454/158

(56) References Cited

U.S. PATENT DOCUMENTS

| | | | |
|---|---|---|---|
| 4,017,736 A | | 4/1977 | Ross |
| 4,203,948 A | | 5/1980 | Brundbjerg |
| 4,223,598 A | * | 9/1980 | Suzuki et al. ............... 454/156 |
| 4,227,446 A | * | 10/1980 | Sone et al. .................. 454/158 |
| 4,493,247 A | | 1/1985 | Wachsman |
| 5,106,512 A | | 4/1992 | Reidy |
| 5,616,172 A | | 4/1997 | Tuckerman et al. |
| 5,656,242 A | | 8/1997 | Morrow et al. |
| 5,742,063 A | | 4/1998 | Scroggins et al. |
| 5,866,076 A | | 2/1999 | Fencl et al. |
| 5,908,494 A | | 6/1999 | Ross et al. |
| 5,925,320 A | | 7/1999 | Jones |
| 5,938,823 A | | 8/1999 | Condit et al. |
| 5,997,619 A | | 12/1999 | Knuth et al. |
| 6,084,250 A | | 7/2000 | Jüstel et al. |
| 6,135,838 A | | 10/2000 | Wang |
| 6,161,910 A | | 12/2000 | Reisenauer et al. |
| 6,268,607 B1 | | 7/2001 | Marsh et al. |
| 6,336,998 B1 | | 1/2002 | Wang |
| 6,402,610 B1 | | 6/2002 | Gloisten |
| 6,437,346 B1 | | 8/2002 | Goudjil |
| 6,503,458 B1 | | 1/2003 | Ogle |
| 6,541,800 B2 | | 4/2003 | Barnett et al. |
| 6,630,678 B2 | * | 10/2003 | Guzorek ................. 250/432 R |
| 2002/0031460 A1 | | 3/2002 | Kulp |
| 2002/0074559 A1 | | 6/2002 | Dowling et al. |
| 2003/0021721 A1 | | 1/2003 | Hall |
| 2003/0039576 A1 | | 2/2003 | Hall |
| 2003/0067008 A1 | | 4/2003 | Srivastava et al. |

FOREIGN PATENT DOCUMENTS

| | | | | |
|---|---|---|---|---|
| JP | 11348552 A | * | 12/1999 | ........... B60H/03/06 |
| JP | 2000127756 A | * | 5/2000 | ........... B60H/03/06 |
| JP | 2001301451 A | * | 10/2001 | ........... B60H/03/06 |
| JP | 2002253662 A | * | 9/2002 | ........... A61L/09/20 |

* cited by examiner

Primary Examiner—Nikita Wells
Assistant Examiner—Erin-Michael Gill
(74) Attorney, Agent, or Firm—Gardner Carton & Douglas LLP

(57) ABSTRACT

A system for cleaning air in a vehicle by ultraviolet light includes an exposure chamber for exposure of air to ultraviolet light. An ultraviolet light source is mounted in the exposure chamber. A collection plenum chamber is connected to a first end of the exposure chamber. An air valve is connected to the collection plenum chamber. An expansion plenum chamber is connected to a second end of the exposure chamber including passages for distribution of air to the exposure chamber. An inlet conduit connected to the expansion plenum chamber directs air to the expansion plenum chamber. The system reliably cleans air and may be packaged so as to be integrated into existing vehicle structures, such as a passenger service unit of an airplane.

11 Claims, 8 Drawing Sheets

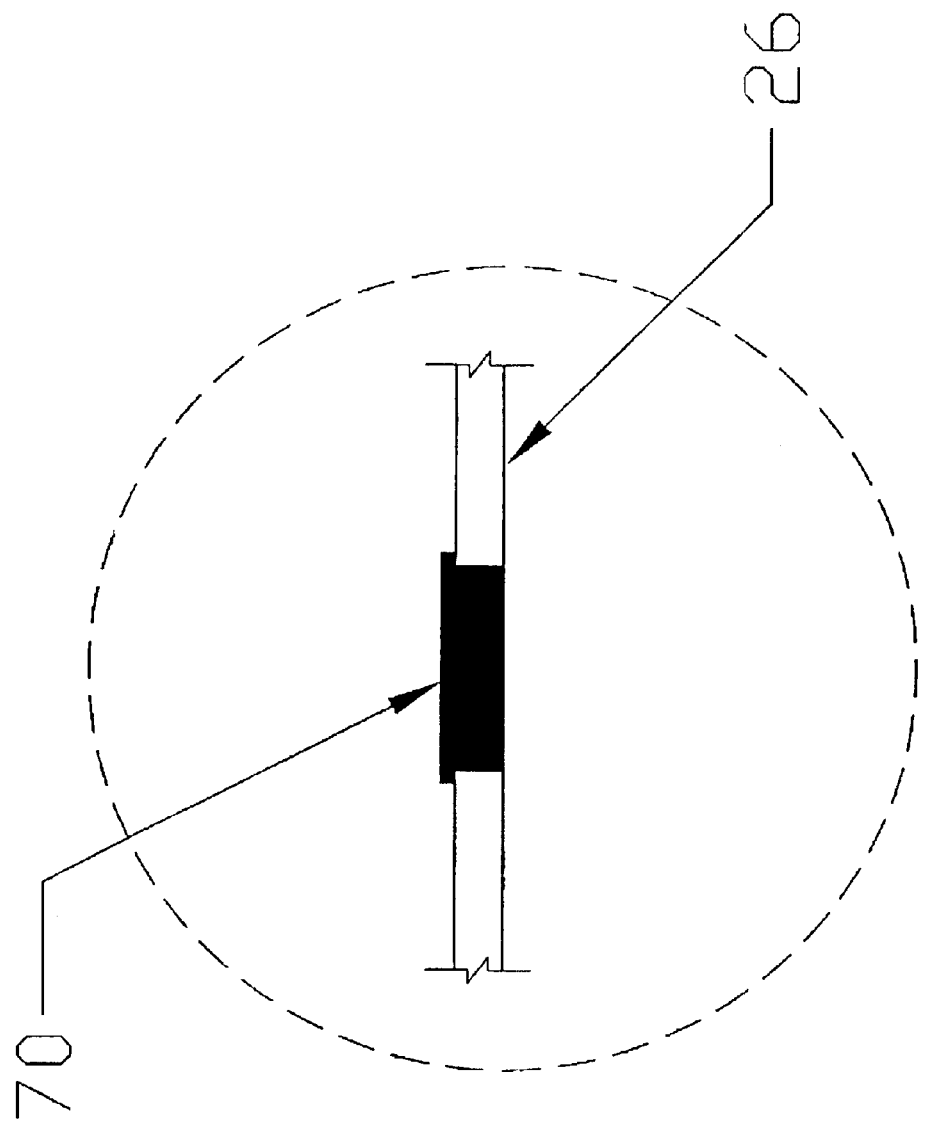

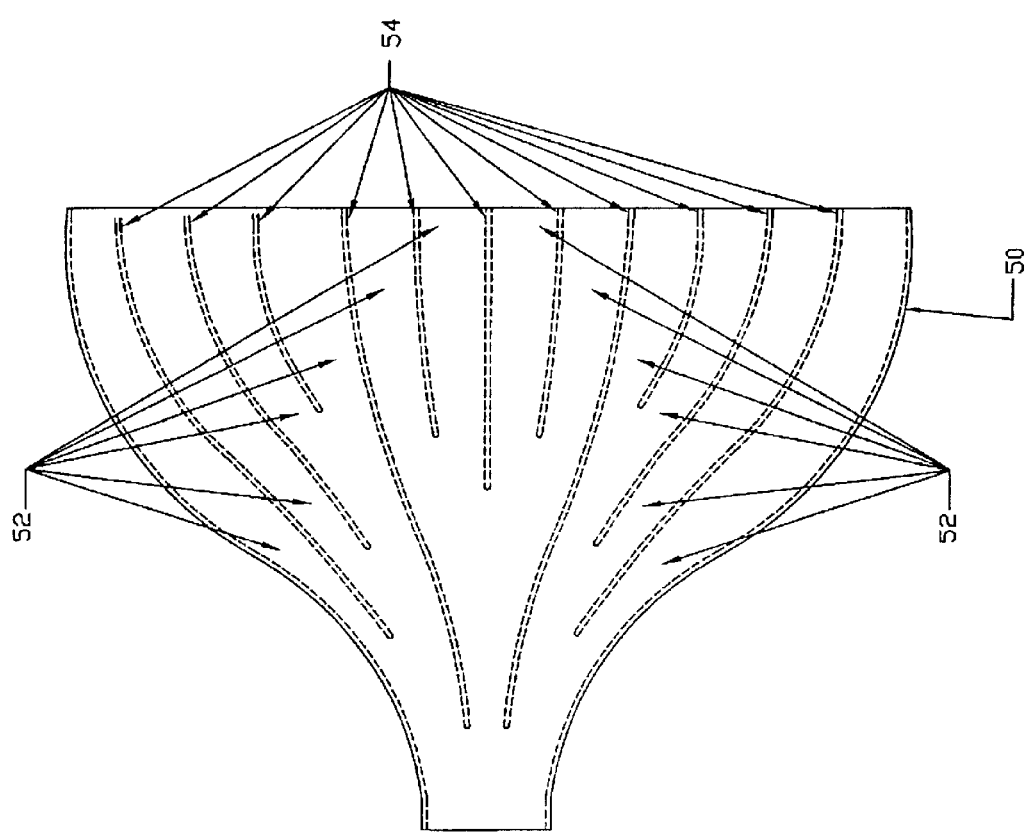

ULTRAVIOLET-LIGHT VEHICLE AIR CLEANING SYSTEM

BACKGROUND OF THE INVENTION

1. Field of the Invention

The present invention relates to an air cleaning system and more particularly to a system which uses ultraviolet light to clean air in a vehicle such as a passenger air plane.

2. The Prior Art

Air outlets are used on commercial transportation vehicles, such as aircraft, railcars, boats, and buses, to provide passengers with a supply of moving air that they can control to improve their comfort. Typically, one air outlet is provided for each passenger location and offers the passenger options to change the volume and direction of air flow. Other conditioning of the air such as modification of temperatures, humidity, and cleanliness is performed in bulk as part of the vehicle's centralized air handling system.

As with all centralized air handling systems that distribute recirculated air among many people, known vehicle air handling systems produce concern that pathogens supplied by one individual can be shared among the group. This concern can degrade the passenger experience, possibly even discouraging some from traveling. Concern is increased further during seasons where a large percentage of the population may be suffering from the common cold and influenza or during periods of atypical outbreaks of pathogens. The concern is especially acute in environments where air is recirculated, such as in aircraft.

It is known to use ultraviolet light to sanitize air or water and air. For example, U.S. Pat. No. 5,742,063 to Seroggins et al. shows a sterilizing unit using ultraviolet light for air ducts in the home or a building. See also, U.S. Pat. No. 5,656,242 to Morrow et al. U.S. Published Patent Application Nos. 2003/0021721 and 2003/0039576 to Hall show an air purification system for an aircraft, vehicle, office or hospital, which combines a filter section with an ultraviolet illumination section and a coating of an antimicrobial agent on surfaces in one or both of these sections.

Although a variety of air sanitizing systems using ultraviolet light are known at the present time, there is still a need for an air cleaning system that allows passengers to access a local ultraviolet air sterilization feature in a vehicle air delivery system so as to eliminate pathogens in the passenger's dedicated air flow and that can be integrated within the mounting outlines of conventional air outlet products in aircrafts and other vehicles.

SUMMARY OF THE INVENTION

A system for cleaning air in a vehicle by ultraviolet light is provided which results in a local area in which the air contains a significantly lower level of pathogens, focused on the passenger location corresponding to that air outlet. The system is potentially helpful to clean air containing not only common pathogens, but also any pathogen which is affected by ultraviolet radiation.

In one aspect, the system includes an exposure chamber for exposure of air to ultraviolet light, an ultraviolet light source mounted in the exposure chamber and a collection plenum chamber connected to a first end of the exposure chamber. An air valve is connected to the collection plenum chamber. An expansion plenum chamber is connected to a second end of the exposure chamber and includes a plurality of passages for distribution of air to the exposure chamber. An inlet conduit is connected to the expansion plenum chamber for directing air to the expansion plenum chamber.

In another aspect, a plurality of selectively operatable subsystems are provided. Each subsystem is adapted for connection to an air delivery system. Each subsystem includes an exposure chamber, an ultraviolet light source, a collection plenum chamber, an air valve, an expansion plenum chamber, and an inlet conduit.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views:

FIG. 2C is an enlarged view of area I of FIG. 2B.

FIG. 3A is a top view of an expansion plenum chamber for the embodiment of FIG. 1.

DETAILED DESCRIPTION OF PREFERRED EMBODIMENTS

Figure 1:
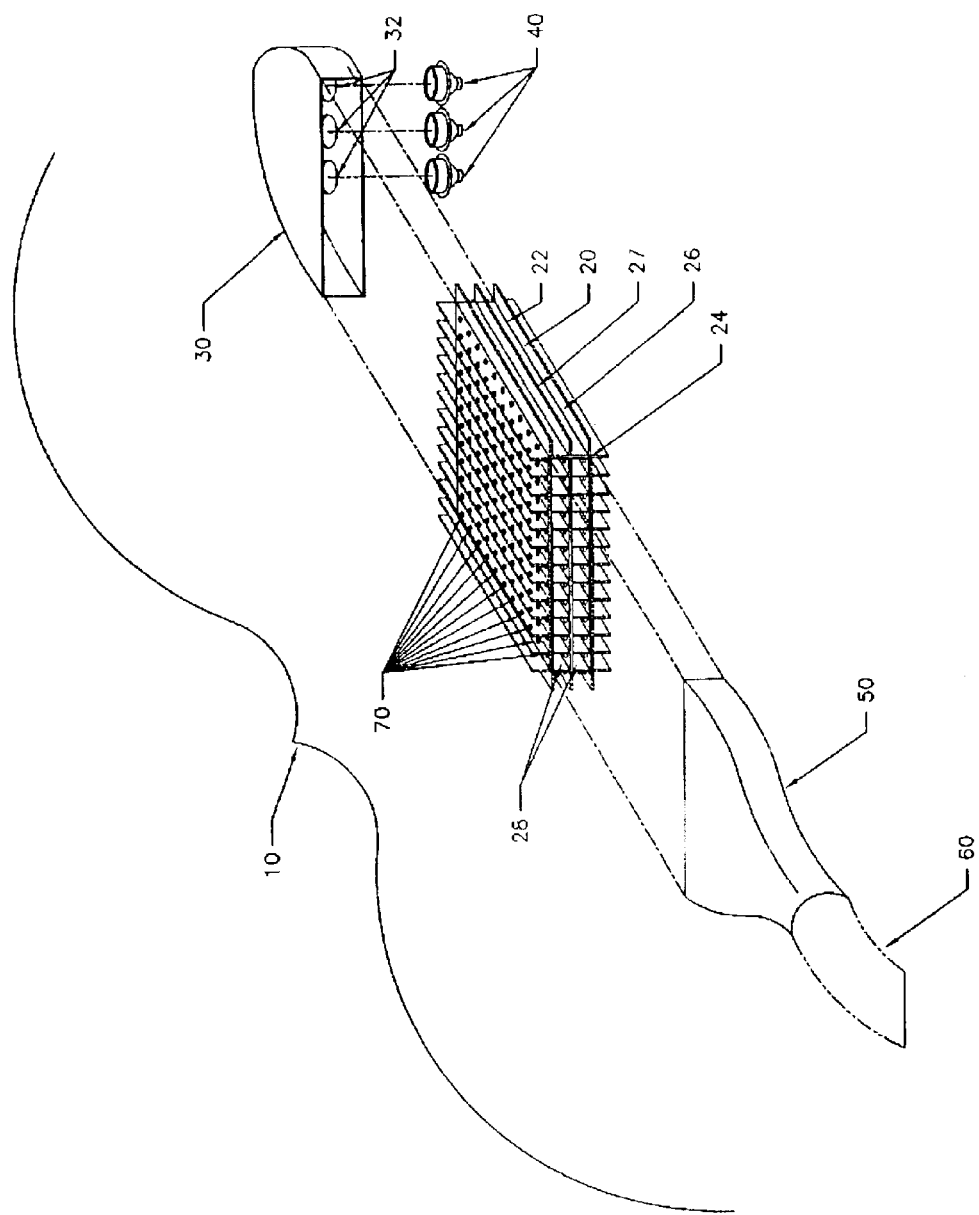
FIG. 1 is an exploded perspective view of an embodiment of the present invention.

Turning now in detail to the drawings, FIG. 1 shows a system 10 for cleaning air in a vehicle by ultraviolet light of a preferred embodiment. The configuration of components will vary with the particular application.

System 10 includes an exposure chamber 20 through which an air stream is caused to flow for exposure of the air to ultraviolet light. Exposure chamber 20 includes a housing 26, for example, rectangular in shape as shown in FIG. 1, and having first and second ends 22, 24. The particular shape of exposure chamber may vary depending on the particular application. Housing 26 preferably is provided with fins 27 which act as a heat sink for dissipation of heat generated within exposure chamber 20. Preferably, exposure chamber 20 is made of an ultraviolet light resistant material such as stainless steel, aluminum or fiberglass. A collection plenum chamber 30 is connected to first end 22 of exposure chamber 20. At least one air valve 40 is connected to collection plenum chamber 30. For example, three air valves 40 are shown in FIG. 1 An expansion plenum chamber 50 is connected to second end 24 of exposure chamber 20. An inlet conduit, for example, a hose 60, is connected to expansion plenum chamber 50.

Figure 2A:
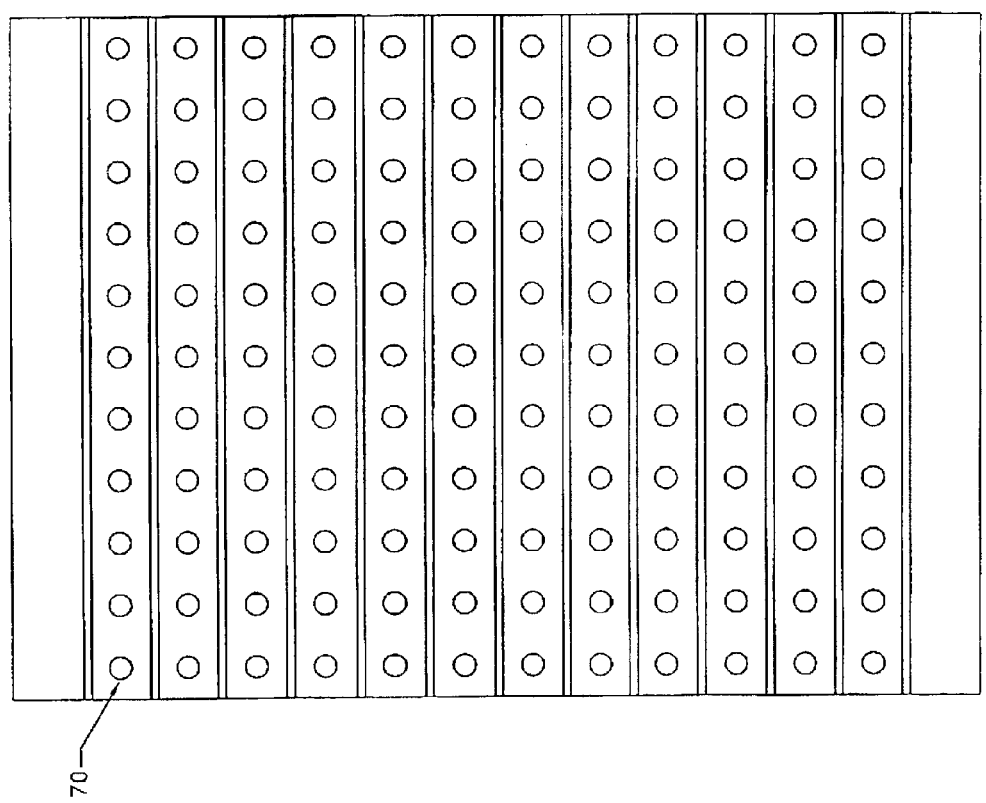
FIG. 2A is a top view of an exposure chamber for the embodiment of FIG. 1.
Figure 2B:
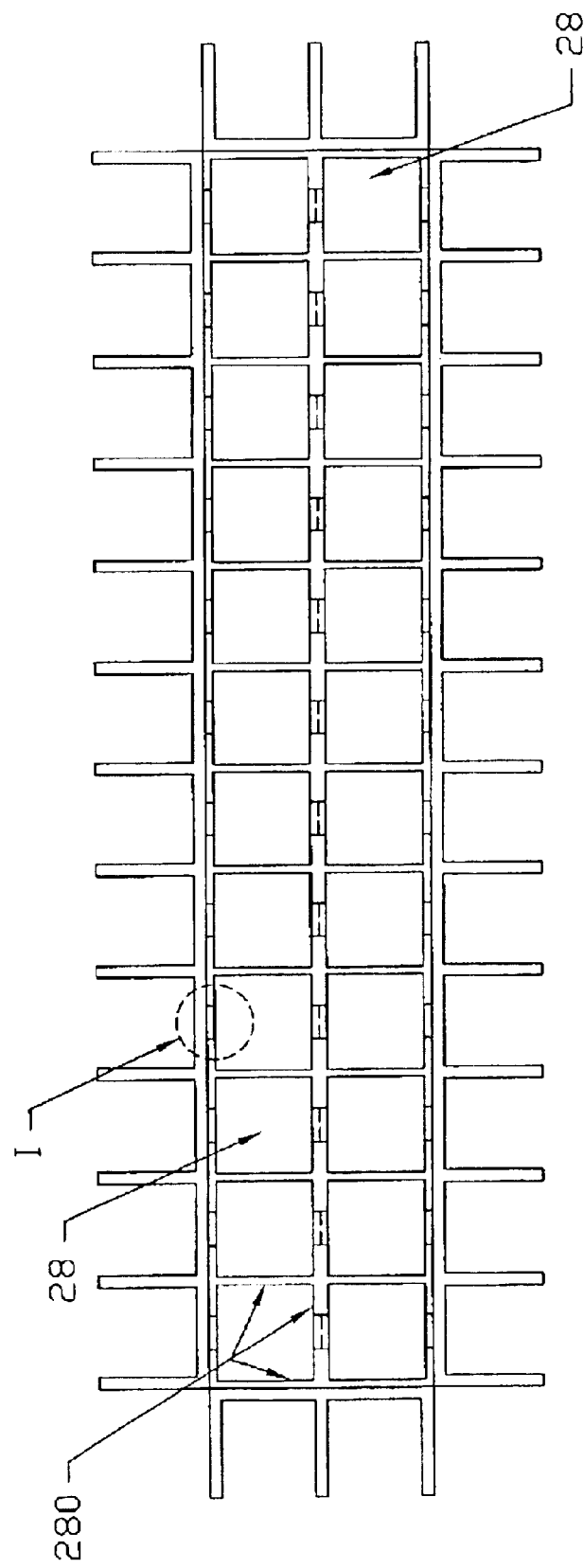
FIG. 2B is an end view of the exposure chamber of FIG. 2A.

An ultraviolet light source, such as ultraviolet (UV) light emitting diodes (LEDs) 70 shown in FIGS. 2A–2B or other UV lamp, is mounted in exposure chamber housing 26. An array of LEDs 70 are shown in FIG. 2A but more or less may be used depending on the particular configuration, dimensions and application. For example, one-hundred seventysix LEDs may be placed within exposure chamber 20. Alternatively, the sterilization function may be accomplished using other sources of ultraviolet light, for example, a low pressure mercury lamp which emits ultraviolet radiation. Additionally, a combination of LEDs and other UV sources may be used.

The most common production source of ultraviolet radiation is the low pressure mercury lamp. These lamps operate in the same manner as fluorescent lamps, using an external power supply to create the electrical discharge through the low pressure mercury vapor in the lamp. A wide variety of such lamps are commercially available. For example, lamps are available in T-5, T-8 and T-12 diameters, ranging in size from 5¾ inches to 47¼ inches long and power outputs of 0.6 to 32 watts.

LEDs which emit UV light are also known. See, e.g. U.S. Pat. No. 6,541,880 to Barnett et al., and U.S. Published Patent Application No. 2003/0067008 to Srivastava et al.

Exposure chamber 20 includes a plurality of subchambers 28, eight being shown in FIG. 1. Each subchamber 28 preferably includes an ultraviolet light source, such as one or more spaced LEDs 70, mounted therein along the length of each subchamber. Expansion plenum chamber 50 may include a plurality of structures partially interrupting air flow through the exposure chamber and causing swirling of air within exposure chamber 20. These structures may be formed by partitions or vanes 54 contained within expansion plenum chamber 50, shown in FIG. 3A, and which act as swirl generators. By increasing the number of times the air is caused to flow past the UV light source, or by using an alternative which increases residence time such as a plenum chamber, the effectiveness of the UV radiation in killing pathogens is increased. Preferably, sharp edges in air flow are avoided to minimize noise, to the extent possible.

Preferably, exposure chamber includes a plurality of internal reflective surfaces adjusted for optimal reflection of ultraviolet light from the ultraviolet light source within the exposure chamber. For example, as shown in FIG. 2B, internal surface 280 of each subchamber 280 may be made reflective, such as by polishing or coating, to maximize the effectiveness of the ultraviolet radiation on pathogens. Surface 280 may also be provided with a germicidal agent that may be refreshed or renewed periodically to further enhance the sterilizing effect on the pathogens.

Because ultraviolet light source 70 is mounted within exposure chamber 20, passenger eyes are not exposed to ultraviolet radiation. When ultraviolet light source 70 is an LED source, drive circuitry for the LEDs preferably includes features such as temperature compensation and current control, such as that described in U.S. Pat. No. 6,161,910 to Reisenauer et al. For lamp products other than LEDs, the drive circuitry preferably includes a circuit which prevents dangerous arcing in the event of a lamp failure. In both cases, the drive circuitry is preferably designed to be driven from power sources readily available in the vehicle.

Preferably, ultraviolet light source 70 includes a plurality of wavelength sources providing different wavelengths of ultraviolet light. For example, each subchamber 28 may include LEDs or ultraviolet lamps having wavelengths 220, 225, 230, 235, 240, 245, 250, 255, 260, 265, 270, 275, 280, 285, 290, 295 and 300 nanometers, or some combination of these wavelengths. By selectively activating one or more of these LEDs or lamps, for example, by a microprocessor or other control system operatively connected thereto, the system will have the ability to maximize lethality to the UV sensitivities of specific bacteria or other pathogens by tuning or mixing several wavelengths from the ultraviolet light source.

Heat generated by the UV source and drive circuit preferably is directed through a heat sink built into the system, such as fins 27 of exposure chamber 20 shown in FIG. 1. The walls of chambers 30 and 50, the mounting structure for the LEDs and UV lamps, and the surfaces of air outlet or valve 40 may also be used to distribute heat so that air temperature is minimally impacted and surface temperatures remain within a safe range. In this way, the temperature of the air will not be raised significantly even though the air is subjected to ultraviolet radiation.

Figure 3B:
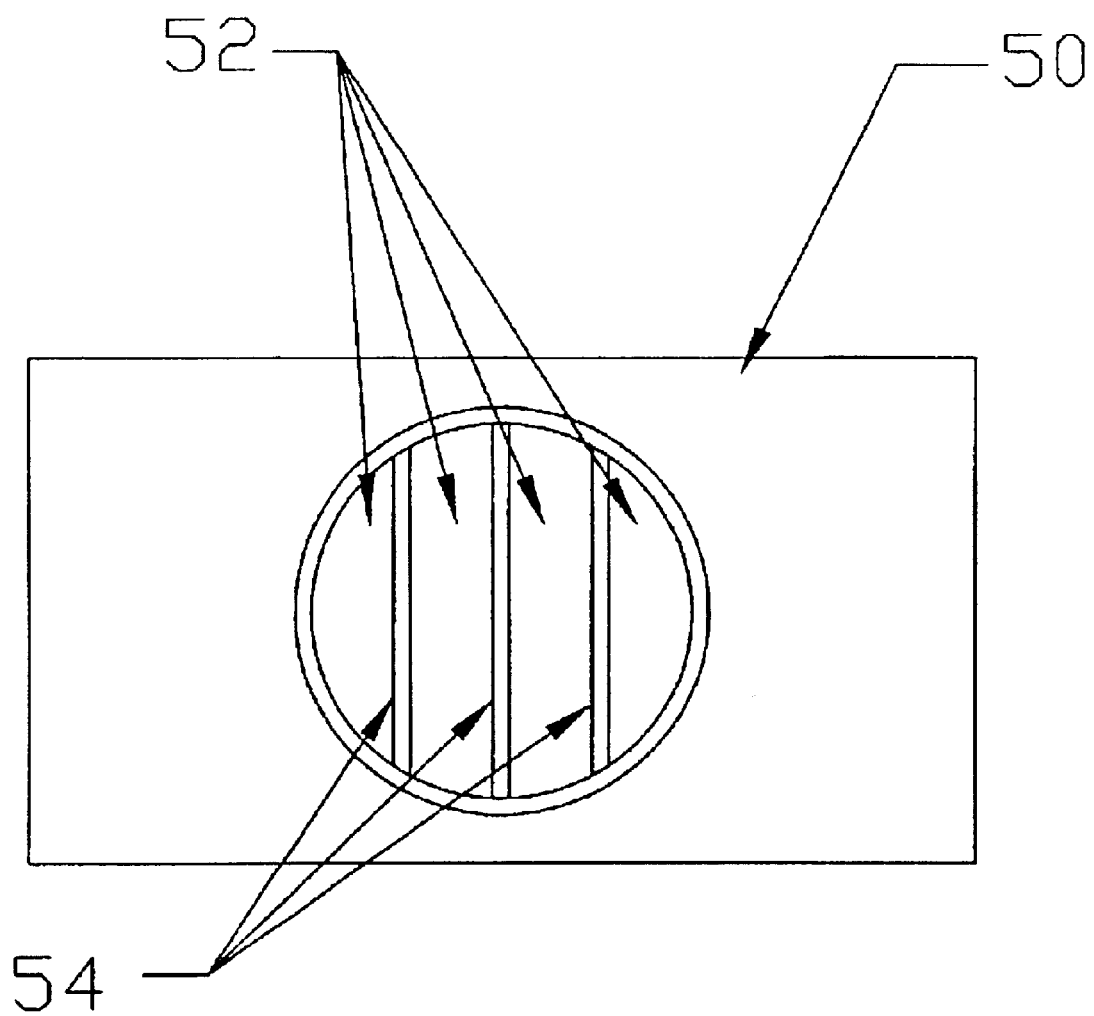
FIG. 3B is an end view of the expansion plenum chamber of FIG. 3A.

As shown in FIGS. 3A and 3B, expansion plenum chamber 50 is preferably vaned, i.e. provided with partitions 54 defining a plurality of passages 52, four being shown in FIG. 3A, for distribution of air to exposure chamber 20. This structure reduces air flow speed and directs air flow past the ultraviolet source in exposure chamber 20 so that sterilization is achieved. By increasing the cross-sectional area, lower air flow results for greater time contact of the air with the UV light source in exposure chamber 20. The particular configuration and dimensions will vary according to the particular application and is dependent on the conditions of the supplied air, such as flow volume and pressure.

Figure 4:
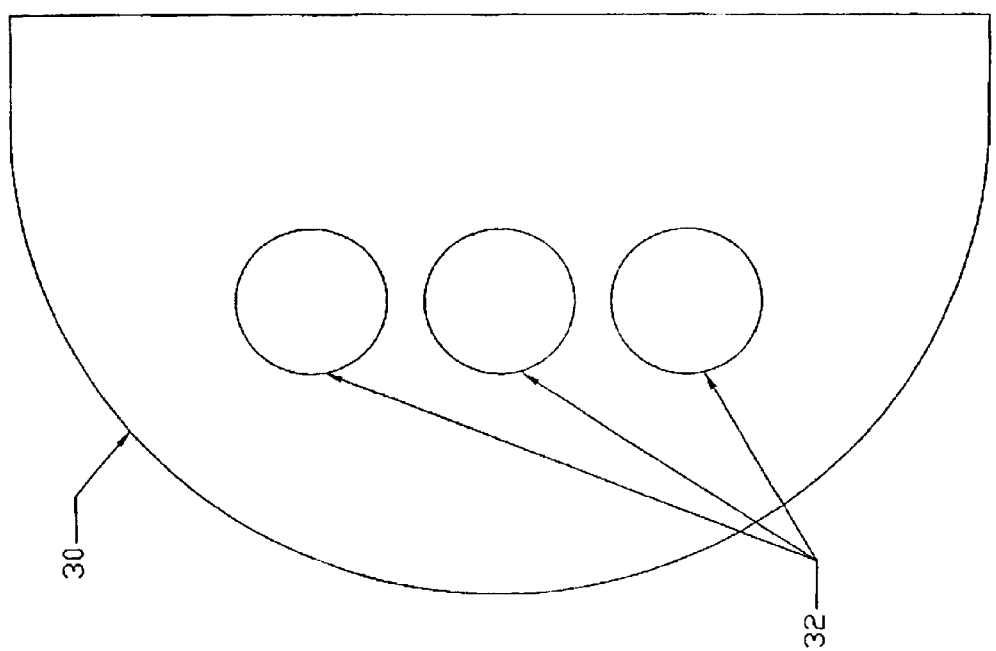
FIG. 4 is a bottom sectional view of a collection plenum chamber for the embodiment of FIG. 1.

FIG. 4 shows collection chamber 30 having an air inlet mounting hole 32 preferably disposed in a bottom portion for mounting each air valve 40, three mounting holes 32 being shown in FIG. 4 for three air valves 40. The size of inlet mounting hole 32 will vary depending on the particular application. Preferably, each air valve 40 includes a nozzle configured to accelerate air flow exiting through air valve 40. For example, the positive shut-off air outlet described in U.S. Pat. No. 6,402,610 to Gloisten may be used.

Activation of ultraviolet light source 70 is preferably accomplished via a switch which may be remote from the actual face of air outlet 40, such as the arm of the seat or among the controls on the overhead passenger service unit where air valve 40 is mounted. While sterilization is active, an indicator or indicators 81 may be provided, such as LED lights that glow, that provide a visual or audio signal to provide feedback that sterilization is taking place. The indicator may be located within or next to air valve 40, or at the switch which activates the feature. There may be an indicator that indicates whether the ultraviolet light source is activated. There may also be indicators provided at each air outlet to provide a visual indication at each passenger location that the air outlet for that location has been activated to dispense clean air. Preferably, by using a flow sensor or a position sensor, the system is designed so that if any outlet is activated by a user, the ultraviolet light source will be activated.

Figure 5:
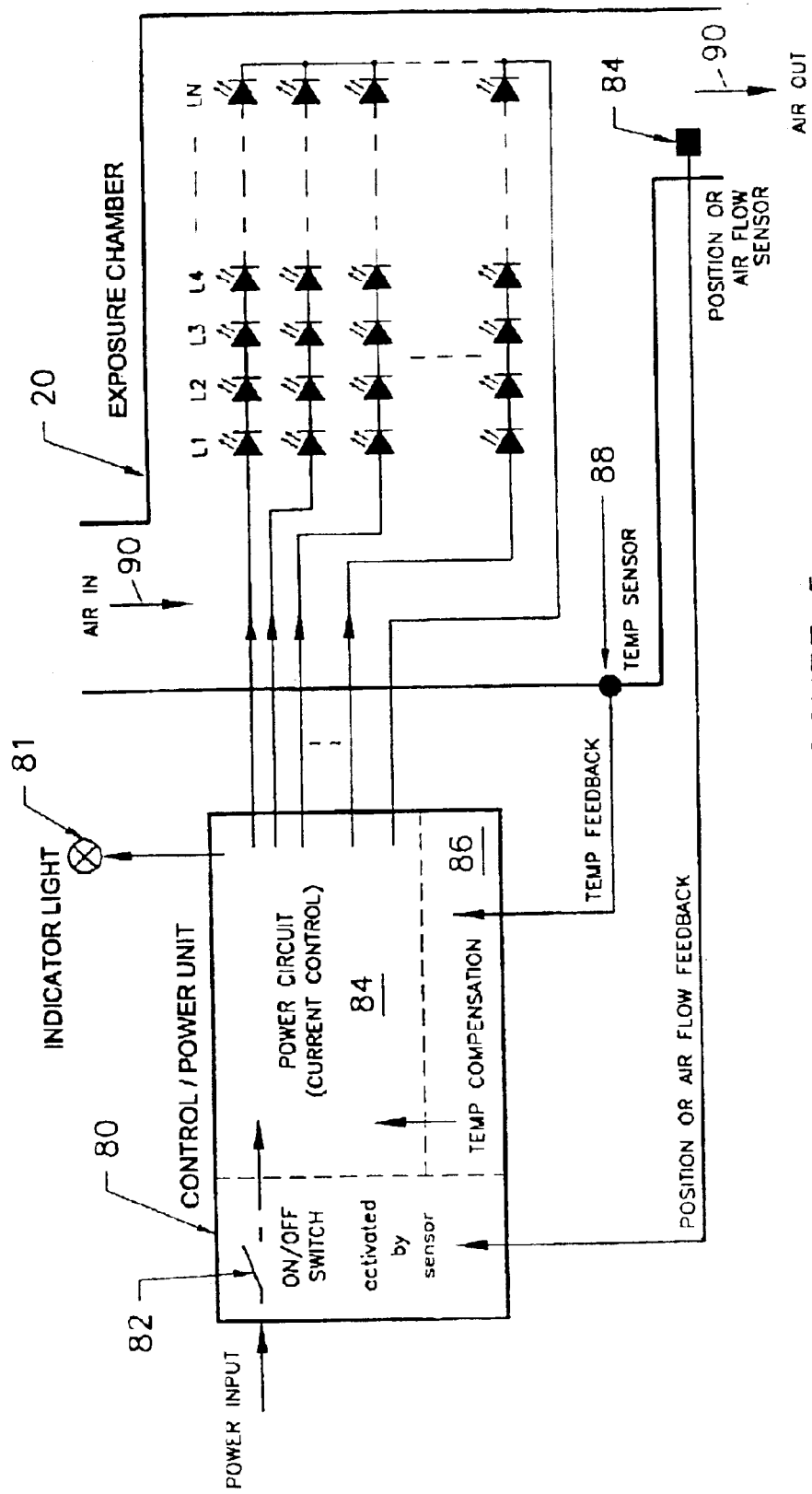
FIG. 5 is a schematic drawing of a control system for the embodiment of FIG. 1.

FIG. 5 is a schematic drawing of a control system for the ultraviolet light source. Control/power unit 80 includes an on/off switch 82 interposed between the vehicle power source and a power circuit 84 for current control. Switch 82 preferably is activated by a sensor 84, such as a position or an air flow sensor. Control/power unit 80 also preferably includes a temperature compensation circuit 86 operatively connected to a temperature sensor 88. Temperature compensation circuit 86 adjust power circuit 84 in response to temperature feedback received from temperature sensor 88. For example, the circuit shown in U.S. Pat. No. 6,161,910 to Reisenauer et al. may be used.

Power circuit 84 drives a plurality of ultraviolet light emitting diodes L1, L2, L3, L4 . . . LN in a plurality of chains of n diodes each disposed in exposure chamber 20. The LEDs may have the same or different wavelengths and may be selectively activated by control/power unit 80 so as to maximize lethality to the UV sensitivity of the particular pathogen as previously described. When the LEDs are activated, power circuit 84 also may activate outside indicator light 81 to advise the user that the cleaning system is working. Alternatively, a sensor may be provided at each outlet that determines whether the particular outlet is open or closed, for example, by detecting air flow or position of the outlet. The sensor is operatively connected to control/power unit 80 so as to turn on the indicator light at the particular outlet when that outlet has been opened. A stream of air 90 in from expansion plenum chamber 50 passes through the area where the light emitting diodes are disposed and exits out to collection plenum chamber 30 and nozzle 40.

Preferably, the system is designed so that it may be provided within the mounting outlines of conventional air outlet products, and if desired, may serve as a drop-in replacement for existing vehicles. For example, the system may be integrated into structures such as a passenger service unit of an airplane. However, the size of the system may be made compatible with any recirculated air system used in vehicles.

Preferably, a plurality of systems 10 are provided in a vehicle's air delivery system, each system being selectively operable by the passenger near the air outlet for that system.

The system preferably uses local positive pressure provided by the air flow of a vehicle's air delivery system in order to reduce influx of the unsterilized air circulating in the vehicle, such as the cabin of a passenger airplane.

By providing a local ultraviolet air sterilization feature at an individual passenger's air outlet, the possibility of residual contamination in the centralized air handling system or introduced between the centralized air handling system and the delivery point is nullified. In addition, the passenger's comfort is increased by their control of the feature and the visible feedback that the system is working on their behalf.

While only a few embodiments of the present invention have been shown and described, it is to be understood that many changes and modifications may be made thereunto without departing from the spirit and scope of the invention as defined in the appended claims.

What is claimed is:

1. A system for cleaning air in a vehicle by ultraviolet light which comprises:
   (a) an exposure chamber for exposure of air to ultraviolet light;
   (b) an ultraviolet light source mounted in said exposure chamber;
   (c) a collection plenum chamber connected to a first end of said exposure chamber;
   (d) an air valve connected to said collection plenum chamber;
   (e) an expansion plenum chamber connected to a second end of said exposure chamber comprising a plurality of passages for distribution of air to said exposure chamber; and
   (f) an inlet conduit connected to said expansion plenum chamber for directing air to said expansion plenum chamber.

2. The system of claim 1 wherein said ultraviolet light source is selected from the group consisting of a low pressure mercury lamp, a light emitting diode, and a combination of a low pressure mercury lamp and a light emitting diode.

3. The system of claim 1 wherein
   (a) said ultraviolet light source comprises a plurality of wavelength sources, each of said wavelength sources providing a respective selected wavelength of ultraviolet radiation; and
   (b) said system further comprises a control system operatively connected to said ultraviolet light source for selectively operating said plurality of wavelength sources to generate ultraviolet radiation of a plurality of wavelengths.

4. The system of claim 1 wherein said expansion plenum chamber comprises a plurality of structures causing swirling of air within said exposure chamber.

5. The system of claim 1 wherein said air value is configured to accelerate air flow exiting said air valve.

6. The system of claim 1 wherein said exposure chamber comprises a plurality of internal reflective surfaces for reflection of ultraviolet light from said ultraviolet light source within said exposure chamber.

7. The system of claim 1 wherein said ultraviolet light source comprises drive circuitry adapted to be operatively connected to a vehicle power source.

8. The system of claim 1 further comprising a heat sink for directing heat away from the flow of air.

9. The system of claim 1 further comprising a switch for selectively activating said ultraviolet light source and an indicator operatively connected to said ultraviolet light source for indicating active cleaning of air through said air valve.

10. The system of claim 1 wherein a plurality of air valves are connected to said plenum chamber.

11. A system for cleaning air in a vehicle by ultraviolet light which comprises a plurality of selectively operable subsystems adapted for connection to an air delivery system, each subsystem comprising:
    (a) an exposure chamber for exposure of air to ultraviolet light;
    (b) an ultraviolet light source mounted in said exposure chamber;
    (c) a collection plenum chamber connected to a first end of said exposure chamber:
    (d) an air valve connected to said connection plenum chamber;
    (e) an expansion plenum chamber connected to a second end of said exposure chamber comprising a plurality of passages for distribution of air to said exposure chamber; and
    (f) an inlet conduit connected to said expansion plenum chamber for directing air to said expansion plenum chamber.

* * * * *